United States Patent [19]

Zorn et al.

[11] Patent Number: 5,776,843
[45] Date of Patent: Jul. 7, 1998

[54] PROCESS FOR THE PRODUCTION OF SPONGIOSA BONE CERAMIC HAVING LOW CALCIUM OXIDE CONTENT

[75] Inventors: Franz Zorn, Ober Ramstadt; Frank Weber, Gross-Umstadt; Antonia Almeida, Reinheim; Ilona Taubert, Seeheim-Jugenheim; Rolf Wagenknecht; Wilhelm Eberle, both of Darmstadt, all of Germany

[73] Assignee: Merck Patent Gesellschaft mit Beschrankter Haftung, Germany

[21] Appl. No.: 836,381
[22] PCT Filed: Nov. 2, 1995
[86] PCT No.: PCT/EP95/04285
  § 371 Date: May 7, 1997
  § 102(e) Date: May 7, 1997
[87] PCT Pub. No.: WO96/14886
  PCT Pub. Date: May 23, 1996

[30] Foreign Application Priority Data

Nov. 10, 1994 [DE] Germany .................. 44 40 149.3

[51] Int. Cl.⁶ .................. C04B 35/00; A61L 27/00
[52] U.S. Cl. .................. 501/1; 623/16; 623/66
[58] Field of Search .................. 501/1, 80; 106/35; 264/56; 623/11, 16, 66

[56] References Cited

U.S. PATENT DOCUMENTS

| | | | |
|---|---|---|---|
| 4,919,751 | 4/1990 | Sumita et al. | 501/1 |
| 5,133,756 | 7/1992 | Bauer et al. | 623/16 |
| 5,306,302 | 4/1994 | Bauer et al. | 623/16 |
| 5,405,390 | 4/1995 | O'Leary et al. | 623/16 |

*Primary Examiner*—Michael Marcheschi
*Attorney, Agent, or Firm*—Millen, White, Zelano & Branigan, P.C.

[57] ABSTRACT

The invention relates to a process for producing spongiosa bone ceramic. Between the demineralization of the bone material and the sintering to a ceramic, an extractive washing operation is carried out using demineralized water, by means of which calcium oxide components are removed from the demineralized bone matrix.

10 Claims, No Drawings

PROCESS FOR THE PRODUCTION OF SPONGIOSA BONE CERAMIC HAVING LOW CALCIUM OXIDE CONTENT

The invention relates to a process for producing spongiosa bone ceramic.

BACKGROUND OF THE INVENTION

It has been known for a relatively long time that mineralized bone which has been sintered to form a ceramic is ideally suited as bone replacement material. With bone ceramic there is naturally a very great degree of correspondence in chemical composition, structural composition and mechanical strength with natural bone. In addition, spongiosa bone ceramic is found to be particularly osteoconductive. The open, interconnecting, trabecular structure of spongiosa bone ceramic promotes the growth of new bone matrix onto and into the ceramic, so that in the course of incorporation there is intensive colonization and therefore integration of the ceramic implant. Bone ceramics produced from bones of animal origin are therefore being increasingly employed as bone replacement materials in osteosynthesis and in the reconstitution of bone defects caused by illness or accident.

The production of bone ceramic from animal bone is generally carried out by first of all freeing selected bones or bone pieces mechanically from all adhering soft parts, then cutting these bones or bone pieces roughly to size by sawing, to give pieces of suitable shape and size, which are then mineralized by the removal of all other organic components. The mineralization process begins first of all with the bones being boiled out several times in water. Subsequent treatment can be carried out, for instance, with fat-dissolving or protein-dissolving solvents, and/or with the aid of hydrogen peroxide, as described for example in EP 0 141 004. Methods which have proved to be particularly simple and effective are those of pyrolytic mineralization, in which the action of heat decomposes the organic component of the bone and the resulting carbon is subsequently burnt to completion in excess oxygen. For the bone pyrolysis, temperatures of between 500° and 1000° C. are common. Following the mineralization of the bone, it is sintered to give the ceramic, with temperatures of between 800° and 1400° C., being common. It is only through sintering that the material acquires the desired ultimate strength. In the course of the procedures mentioned, particular care must be taken to ensure that the porous structure of the original bone is retained as far as is possible. For the conversion of spongiose bone material to spongiosa bone ceramic, a preferred option is to proceed in accordance with a process set out in DE 37 27 606, in which a specific temperature regime and reductive or oxidative character of the atmosphere enables particularly gentle pyrolysis.

It has been found that bone ceramic has a tendency towards uncontrolled instability if the principal phase, hydroxyapatite, exists alongside notable quantities of calcium oxide, which can be detected, for instance, by X-ray analysis. This is the case when the content of calcium oxide is more than 5%. The ingress of water, for example in the form of atmospheric humidity in the course of unprotected storage or in the organism after the implant procedure, is accompanied by successive transformation of calcium oxide to calcium hydroxide, which entails a considerable increase in volume. Depending on the proportional content, this process may extend up to complete breakdown of the ceramic. The proportion of calcium oxide in the bone ceramic is a natural parameter and may vary with the individual nature and breed of animal. The calcium oxide is formed by the calcium carbonate which is naturally present in the bone undergoing conversion, in the course of pyrolysis and sintering, to calcium oxide.

DE 40 28 683 proposed treating the mineralized bone material, prior to sintering, with an aqueous solution of an organic acid, especially citric acid. This step leaches calcium oxide components out of the material, so that the bone ceramic obtained after sintering has, according to X-ray analysis, a hydroxyapatite apatite content of more than 99%.

Although this procedure is highly effective and leads to a useful stable bone ceramic, it is not without disadvantages. These disadvantages lie firstly in the operative area of the process regime. Thus, in the case of pyrolytic mineralization in particular, the material must first be cooled to room temperature again in order to enable the acid treatment and the necessary rinsing operations to be carried out. After this, the material must be heated up again from scratch for sintering. These operations are time-consuming and energy-intensive. In addition, the preparation and consumption of the acid solution and the consumption of rinsing water for washing the material to neutrality increase the production costs. Furthermore, the control and monitoring of the acid treatment step is not simple. On the one hand, it must be ensured here that virtually all of the calcium oxide is leached out, while on the other hand little or none of the hydroxyapatite matrix must be attacked by the acid. The spongiose fine structure has at this point in the process not yet undergone sufficient solidification, and is therefore highly sensitive. An object of the present invention was therefore to lessen the abovementioned disadvantages of the prior procedure.

SUMMARY OF THE INVENTION

Surprisingly it has now been found that calciumoxide components present in mineralized bone matrix can readily be removed if the bone matrix is subjected to a washing operation with demineralized water at a temperature of from 10° to 80° C. over a period of from 4 hours to 7 days. The leaching of calcium oxide using acid, especially aqueous citric acid solution, has therefore been found to be unnecessary.

The invention thus provides a process for the production of spongiosa bone ceramic, in which process spongiose bones cut into pieces are demineralized by the removal of all organic constituents and then the mineral bone matrix is sintered to the ceramic, which process is characterized in that, in order to remove calcium oxide components from the demineralized bone matrix, the bone matrix, prior to sintering is subjected to extractive washing with demineralized water at a temperature of from 10° to 80° C. over a period of from 4 hours to 7 days.

The process according to the invention is carried out in practice in complete analogy to that known from DE 40 28 683. The only difference here is that the acid treatment step provided between the demineralization of the bone material and the sintering to a ceramic is replaced by a treatment with demineralized water. Demineralized water is known per se and is readily available. It can be prepared in any desired quantity by generally known methods from natural water, for example by single or multiple distillation and/or removal of the dissolved mineral salts using ion exchanges. In general, demineralized water has a slightly acid pH of about 6.0. It is assumed that this slightly acid character of the demineralized water favors the extractive washing of calcium oxide from the mineralized bone matrix.

For the extractive washing operation it is sufficient to convey the mineralized bone material, cut into pieces, into an appropriately dimensioned bath of demineralized water and to leave it there for a time which appears to be sufficient and expedient at an appropriate temperature. Circulation or agitation of the water bath may contribute to leaching out the soluble constituents. It has been found adequate and expedient to employ a ratio of 10 l of water per kg of bone material and a duration of treatment of from 4 hours to 7 days at a bath temperature of between 10° and 80° C. Changing the washing water one or more times, or continuous flushing with fresh demineralized water, has a beneficial effect on the result and may shorten the treatment time. The procedure indicated enables virtually all of the content of calcium oxide present or to be expected in the bone matrix to be removed, essentially without residue. In general, the natural amount of calcium oxide in the bone varies between 5 and 10%. Through X-ray analysis on the ceramic ultimately obtained, it is found that the material has a hydroxyapatite content of more than 95% and in general of 97–99%. Calcium oxide can be detected only in traces if at all.

The process according to the invention enables a saving of not inconsiderable quantities of the acid which as hitherto been required to achieve a comparable result. In addition, after-rinsing operations to wash the material to neutrality are dispensed with, therefore affording additional savings in cost and time. Moreover, the process according to the invention is substantially more gentle, since the hydroxyapatite matrix is not attacked by the treatment with demineralized water.

After the end of the extractive washing operation, the pieces are dried and then sintered to ceramic in a conventional manner.

EXAMPLE

Raw heads of bone, freed from soft parts, from newly slaughtered cattle are sawn into rectangular pieces with dimensions of roughly 30×30×100 mm which are boiled out with water three times for about 1 hour.

The bone pieces are then dried at 110° C. for 6 hours. They are then heated under a nitrogen atmosphere to 450° C. over the course of 9 hours. During a subsequent 20-hour heating period from 450° C. to 6000° C., the atmosphere is changed over in linear progression to atmospheric oxygen, and heating is continued to 900° C. over the course of 5 hours. After cooling, the pieces are placed into a bath of demineralized water (10 l per kg of bone material) and treated in the agitated bath at a temperature of 20° C. for a period of 48 hours. After this treatment, the pieces are rinsed three times with demineralized water.

For final sintering, the pieces are heated to 1250° C. over the course of 21 hours, held at this temperature for 3 hours, and then allowed to cool down.

The resulting bone ceramic pieces exhibit the unchanged porous structure of the original spongiose bone. According to X-ray analysis the ceramic has a hydroxyapatite content of about 99%.

We claim:

1. In a process for the production of spongiosa bone ceramic, comprising demineralizing spongiose bones cut into pieces by removing all organic components and sintering the de-mineralized bone to produce a ceramic, the improvement comprising removing calcium oxide components from the bone pieces by subjecting the bone pieces, prior to sintering, to extractive washing with demineralized water for a time and at a temperature effective to remove calcium oxide.

2. A process for the production of a spongiosa bone ceramic, comprising sintering a bone matrix that has been demineralized by extractive washing the matrix with demineralized water in order to remove calcium oxide.

3. A process according to claim 2, wherein the extractive washing is conducted at 10°–80° C. for 4 hours to 7 days.

4. A process according to claim 2, wherein sintering is conducted at 800° to 1400° C.

5. A process according to claim 2, wherein 10 l water per kg bone material is used for the extractive washing.

6. A process according to claim 2, wherein the extractive washing is conducted by continuous flushing of the bone matrix with fresh demineralized water.

7. A process according to claim 2, wherein the demineralized water is changed at least once during washing.

8. A process according to claim 2, wherein the bone matrix contains at least 95% hydroxyapetite subsequent to extractive washing.

9. A process according to claim 2, wherein the bone matrix contains at least 97–99% hydroxyapetite subsequent to extractive washing.

10. A process according to claim 2, wherein the bone ceramic is not treated with organic acid.

* * * * *